(12) United States Patent
Aldrich et al.

(10) Patent No.: US 7,684,865 B2
(45) Date of Patent: Mar. 23, 2010

(54) METHODS AND APPARATUS FOR TREATMENT OF OBESITY

(75) Inventors: William Aldrich, Napa, CA (US); David Miller, Palo Alto, CA (US)

(73) Assignee: Endovx, Inc., Napa, CA (US)

( * ) Notice: Subject to any disclaimer, the term of this patent is extended or adjusted under 35 U.S.C. 154(b) by 1537 days.

(21) Appl. No.: 10/389,236

(22) Filed: Mar. 14, 2003

(65) Prior Publication Data
US 2004/0181178 A1 Sep. 16, 2004

(51) Int. Cl.
*A61N 1/08* (2006.01)
(52) U.S. Cl. .......................... 607/40; 607/112
(58) Field of Classification Search ............ 607/40, 607/112; 600/554, 561
See application file for complete search history.

(56) References Cited

U.S. PATENT DOCUMENTS

| | | | |
|---|---|---|---|
| 5,188,104 A | 2/1993 | Wernicke et al. | |
| 5,263,480 A | 11/1993 | Wernicke et al. | |
| 5,807,285 A | 9/1998 | Vaitekunas et al. | |
| 6,197,022 B1 | 3/2001 | Baker | |
| 6,405,732 B1 | 6/2002 | Edwards et al. | |
| 6,826,428 B1 * | 11/2004 | Chen et al. | 607/40 |
| 7,072,720 B2 * | 7/2006 | Puskas | 607/118 |
| 7,310,552 B2 * | 12/2007 | Puskas | 607/2 |
| 2002/0087192 A1 | 7/2002 | Barrett et al. | |
| 2003/0023287 A1 | 1/2003 | Edwards et al. | |
| 2004/0082859 A1 | 4/2004 | Schaer | |

FOREIGN PATENT DOCUMENTS

| | | |
|---|---|---|
| WO | WO 00/69376 | 11/2000 |
| WO | WO 01/00273 A1 | 1/2001 |
| WO | WO 01/22897 A1 | 4/2001 |

OTHER PUBLICATIONS

"The Role of the Gastric Afferent Vagal Nerve in Ghrelin-Induced Feeding and Growth Hormone Secretion in Rats," Date, Yukari et al., Gastroenterology 2002; 123:1120-1128.
"Ghrelin Acts in the Central Nervous System to Stimulate Gastric Acid Secretion," Date, Yukari et al., Biochem. and Biophys. Res. Communications, 280, 904-907 (2001).
"Gastroplasty for Obesity: Long-Term Weight Loss Improved by Vagotomy," Kral, John G. et al., World J. Surg. 17, 75-79 (1993).
"Surgical Treatment of Obesity," Kral, John G. MD, PhD, Medical Clinics of North America, vol. 73, No. 1, Jan. 1989.
"Behavioral effects of vagotomy in humans," Kral, John G., J. of Autonomic Nervous System, 9 (1983) 273-281.
"Truncal Vagotomy in morbid obesity," Kral, John G. et al., Int'l J. of Obesity (1981) 5, 431-435.

* cited by examiner

*Primary Examiner*—Carl H. Layno
*Assistant Examiner*—Tammie K. Heller
(74) *Attorney, Agent, or Firm*—Orrick, Herrington & Sutcliffe LLP

(57) ABSTRACT

Method and apparatus for treating obesity by use of transesophageal delivery of energy to interrupt the function of vagal nerves. The energy, which may be highly focused ultrasound energy or other types of energy is delivered through the wall of the esophagus by a device placed in the esophagus. The energy delivered is sufficient to ablate a vagal nerve on the outer wall of the esophagus.

22 Claims, 9 Drawing Sheets

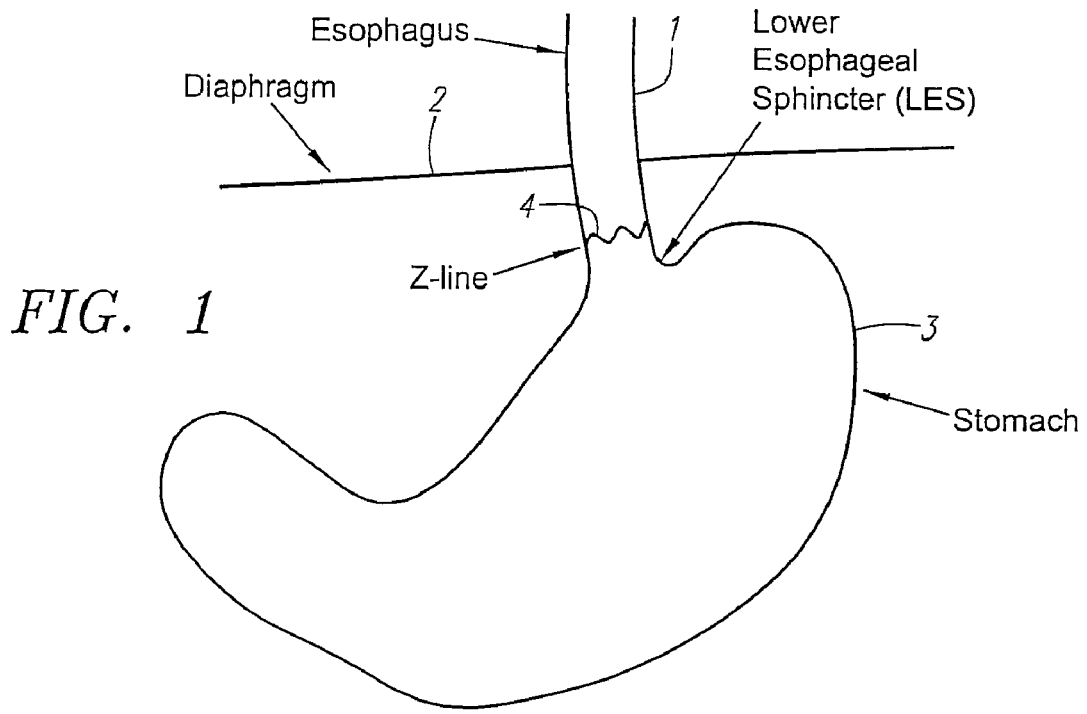
FIG. 1  GENERAL STOMACH ANATOMY
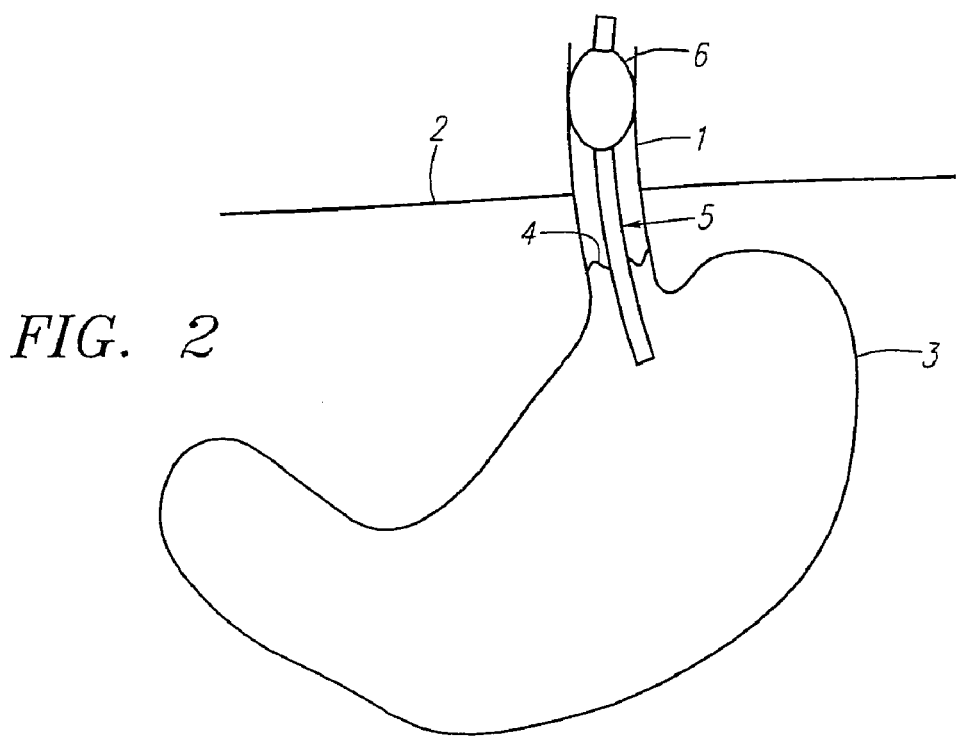
FIG. 2  BALLOON POSITIONING - SINGLE SUPERIOR

BALLOON POSITIONING - SINGLE LOWER

FEET POSITIONING

BITE BLOCK
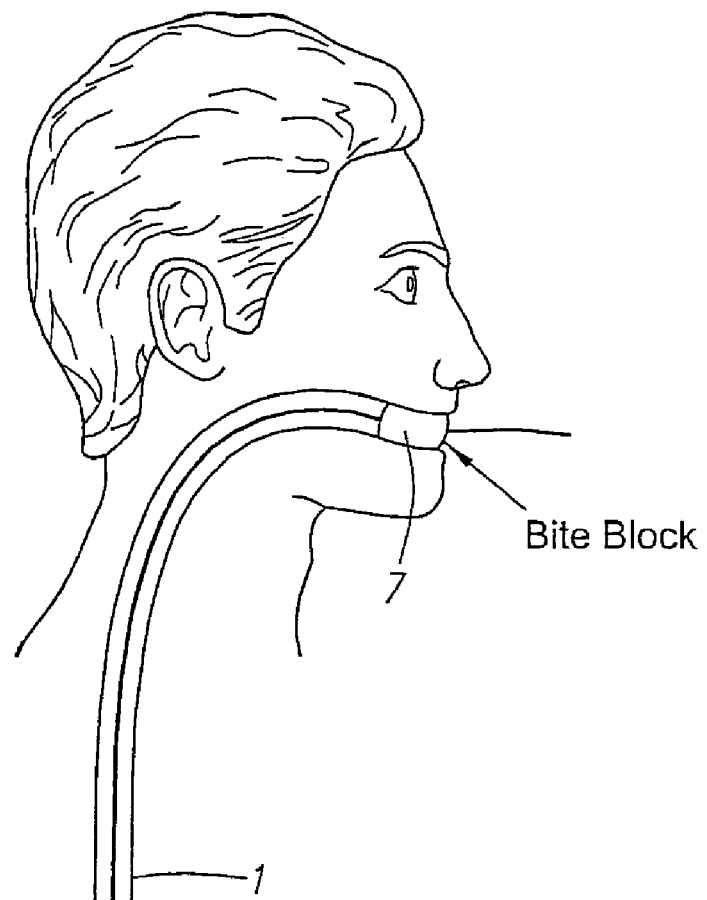
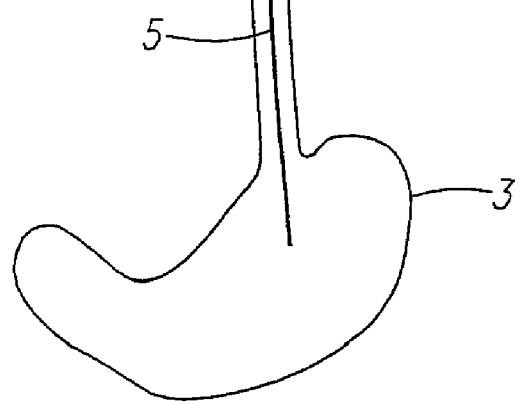
FIG. 5

COMPLETE CIRCUMFERENCE ABLATION

SECTOR SCAN/ABLATION

DEVICE WITH UNDEPLOYED BALLOONS

DEVICE WITH DEPLOYED BALLOONS

METHODS AND APPARATUS FOR TREATMENT OF OBESITY

BACKGROUND OF THE INVENTION

Obesity has become an ever-increasing health problem. While such voluntary weight reduction programs as dieting and exercise have been helpful for some, many obese persons have required surgery to address their obesity problem. Two such surgical procedures are vertical banded gastroplasty (VBG) and the Roux-en-Y gastric bypass procedure. Both such procedures are now well known, but they are invasive in nature and involve reducing the size of the stomach. While these procedures have demonstrated a reasonable level of efficacy, there has remained a need for an obesity treatment that would not involve the patient trauma of invasive surgery and would yet be effective.

SUMMARY OF THE INVENTION

The present invention is, in general, directed to the treatment of obesity by creating an interruption of the vagal nerve, preferably in the region of the esophagus, by minimally or noninvasive means. While the present invention is not to be tied to any particular theory of operation, it appears that a hunger signal is expressed by ghrelin, a peptide primarily produced in the stomach, and transmitted to the brain through the vagal nerve. The literature e.g., "The Role of the Gastric Afferent Vagal Nerve in Ghrelin-Induced Feeding and Growth Hormone Secretion in Rats," *Gastroenterology* 2002: 123:1120-1128 (October 2002) by Yukari Date et al. and "Gastroplasty for Obesity: Long-term Weight Loss Improved by Vagotomy," *World Journal of Surgery*, Vol. 17, No. 1, January/February 1993, by Kral et al., supports this theory. The Date et al. article concluded that blockade of the gastric vagal afferent abolished ghrelin-induced feeding in rats and the Kral et al. article concluded that vagotomy combined with gastroplasty was more effective in controlling weight loss than gastroplasty alone. These articles are incorporated by reference herein.

More specifically, a preferred embodiment of the present invention is directed to interrupting the function of the gastric vagal nerve in the region of the esophagus by using an ablating or other nerve dysfunction causing device installed in the esophagus which delivers ablating energy to one or more vagal nerve branches in a transesophageal manner. The anatomy of the vagal nerve complex varies somewhat from person to person, but, common to all is a structure comprising multiple vagal nerve branches located on the outer wall of the esophagus which run generally longitudinally along the esophagus wall. The present invention contemplates interrupting the function of one or more vagal nerve branches in a transesophageal manner by using various types of energy including radio frequency (RF) energy, high intensity ultrasound, high intensity focused ultrasound, and other types of energy as described in more detail below.

Typically, there are two main branches, or trunks, of the vagal nerve which are located approximately 180° from each other on the outer wall of the esophagus. Depending on patient needs, it may be sufficient to interrupt only a portion of the fibers in the nerve. In this regard, it is to be noted that, in general, myelinated vagal nerve fibers, i.e., fibers that have an outer coating, are efferent. In contrast, afferent vagal nerves are unmyelinated and have no outer covering. For some patients, it may be sufficient to interrupt the function of only the afferent vagal fibers.

The ultimate objective is, of course, substantial weight loss by the patient as a result of a substantial decrease in the ghrelin hunger signal transmitted through the vagal nerve branches. Thus, the success of the procedure described herein will, to some extent, be patient-dependent and, in some patients, it may be necessary to interrupt both the afferent and efferent vagal branches.

In practicing the present invention, the energy source may be installed in the esophagus through the throat, but nasogastric access through the nose and extracorporeal application are also contemplated. The energy may be delivered to the vagal nerve through the esophagus wall, e.g., when ultrasound is used, or by causing an energy delivery device, e.g., an electrode to be passed through the wall of the esophagus.

Still other energy sources can be used to interrupt the function of the vagal nerves including thermal, microwave, laser and cryogenic energy. Alternatively, the vagal nerve function can be interrupted by transesophageal delivery of a neurotoxin such as capsaicin, atropine, or botulinum toxin. Still further, mechanical means can be used to crush the vagal nerve, e.g., with a clip or pincer, or the vagal nerve can be cut transesophageally with an appropriate cutting instrument. In a preferred embodiment of the present invention, the vagal nerve will be interrupted in the vicinity of the zig-zag line, also known as the Z-line, which is genreally located in the lower esophagus between the cardiac notch of the stomach and the diaphragm.

DESCRIPTION OF THE DRAWINGS

FIG. 1 is a diagrammatic illustration of the general anatomy of the stomach and esophagus.

FIG. 2 illustrates positioning of an ablation device using a single balloon installed above the diaphragm.

FIG. 5 illustrates a positioning device using a bite block.

DETAILED DESCRIPTION OF THE INVENTION

Before turning to the manner in which the present invention functions, it is believed that it will be useful to briefly review the anatomy of the stomach and the esophagus. The esophagus is a muscular tube that carries food from the throat to the stomach and which passes through the diaphragm. The top end of the esophagus is the narrowest part of the entire digestive system and is encircled by a sphincter (circular muscle) that is normally closed but can open to allow the passage of food. There is a similar sphincter at the point where the esophagus enters the stomach. The walls of the esophagus consist of strong muscle fibers arranged in bundles, some circular and others longitudinal. The inner lining of the esophagus consists of smooth squamous epithelium (flattened cells).

As shown in FIG. 1, the esophagus 1 extends through the diaphragm 2 into the stomach 3. Vagal nerve branches extend from the stomach along the outer wall of the esophagus to the brain. At the lower end of the esophagus, the juncture of the esophageal and gastric mucosa forms a zig-zag line 4, usually referred to as the Z-line. In the area extending from the diaphragm to a point below the Z-line, there is a subhiatal fat ring which surrounds the outer wall of the esophagus. The vagal nerve branches run between the outer wall of the esophagus and the hiatal fat ring in this area. This anatomy is well understood by those skilled in the art and a more detailed description can readily be found in a standard work such as *Gray's Anatomy*.

Figure 3:
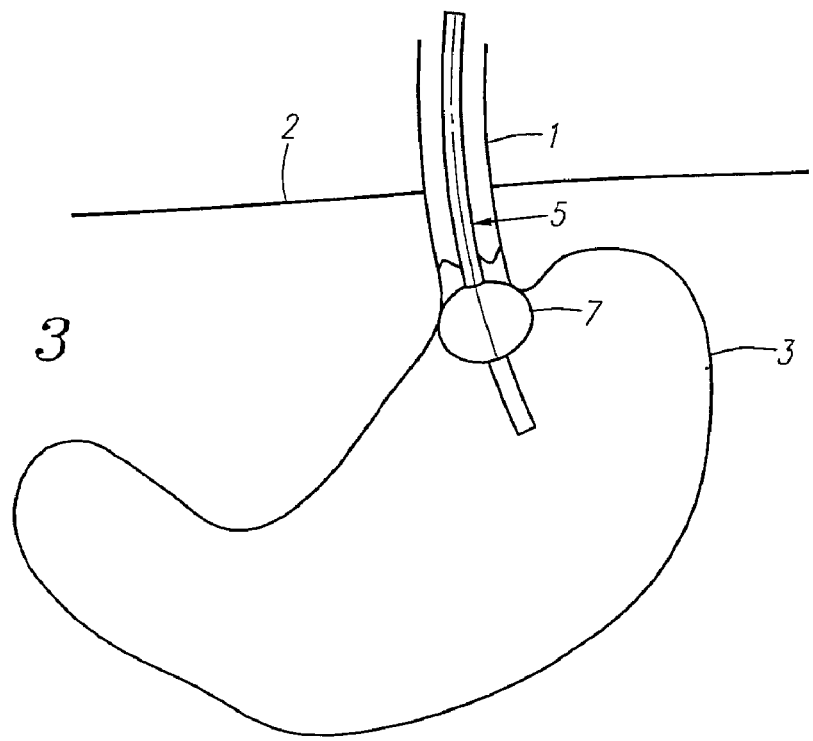
FIG. 3 illustrates positioning the ablation device using a balloon which is inflated in the stomach.
Figure 4:
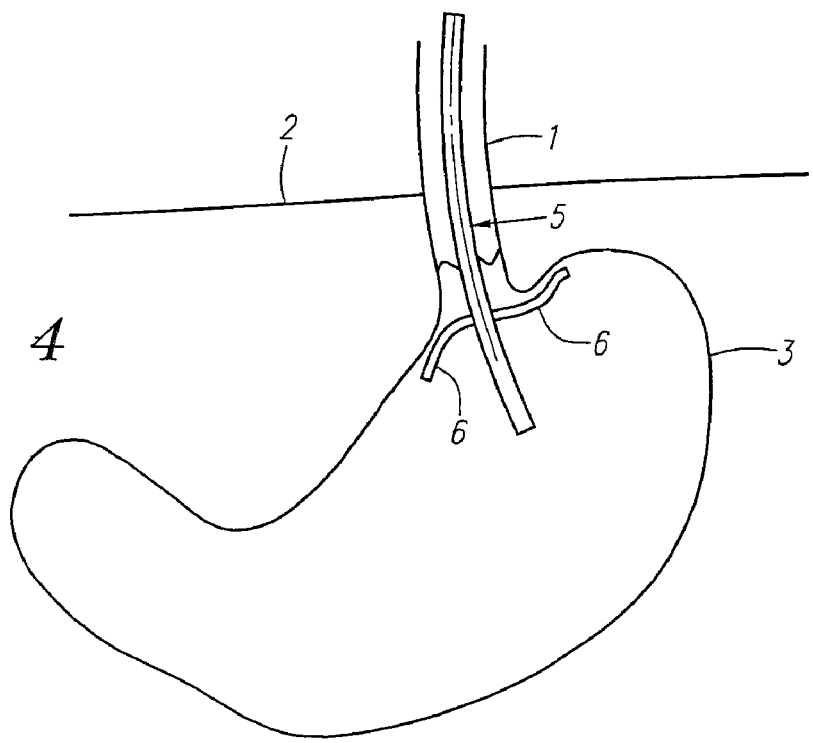
FIG. 4 illustrates a positioning device using radially extending feet.
Figure 6:
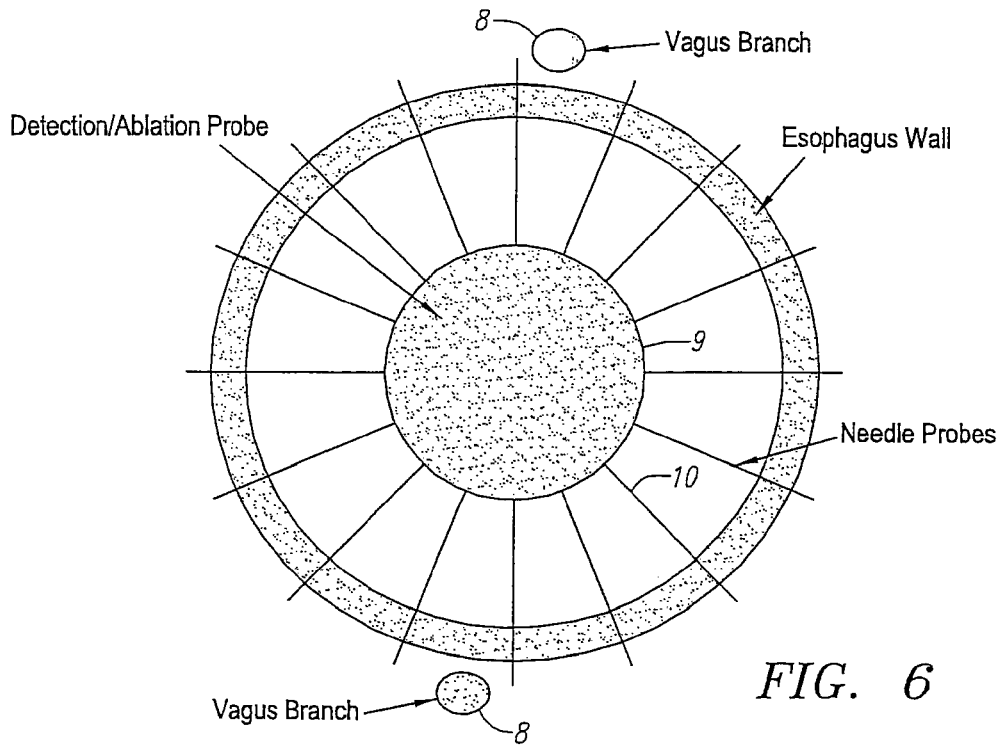
FIG. 6 is a diagrammatic illustrate of the use of needles or electrodes to detect and ablate around the circumference of the outer surface of the esophagus in a manner designed to interrupt all vagal nerve branches.

FIG. 2 illustrates in a diagrammatic manner an ablation device 5 which is held in place by balloon 6 which is inflated inside the upper portion of the esophagus. FIG. 3 illustrates positioning the ablation device 5 with balloon 7 which is inflated inside stomach 3. FIG. 4 illustrates positioning the ablation device 5 with feet 6 which pass through the esophagus folded against the ablation device 5 and then are extended inside stomach 3. FIG. 5 illustrates the use of a bite block 7 to position the ablation device 5 in stomach 3. FIG. 6 is a diagrammatic transverse cross section of the esophagus showing, in diagrammatic form, the esophagus wall 1, vagal nerve branches 8, a detection/ablation device 9 having needle probes 10. As shown, the needle probes 10 extend through the wall of the esophagus and can be used both to locate the vagus nerve and to ablate it. For detection purposes, the needle probes 10 are connected to an exterior control unit that detects and displays nerve activity in a manner well known to those skilled in the art. Once a vagal nerve is detected by a needle probe by sensing the activity of the nerve upon contact, the adjacent needle probes are energized and act in the manner of bipolar cautery probes which ablate the nerve and any other tissue between the needle probes. Preferably, the needle probes are designed in such a manner that they are held within the body of the ablation device until the device reaches its desired location. The needle probes can then be extended to penetrate the wall of the esophagus once the device has been positioned. Preferably, the needle probes are designed so that the electric current flows only at their tips so that the depth of the cautery can be focused to minimize damage to the esophagus. Cosman U.S. Pat. No. 4,565,200, Rydell U.S. Pat. No. 5,007,908, Edwards U.S. Pat. No. 5,370,675 and Edwards U.S. Pat. No. 6,129,726, each of which is incorporated by reference herein, disclose various types of electrode needle probe devices which can be used to deliver RF energy to tissue located within the body. Each of these patents discloses a device in which the needle probes are contained within the device until it has reached its desired location, at which time the needle probes are deployed to contact the tissue to which energy is to be delivered.

Figure 7:
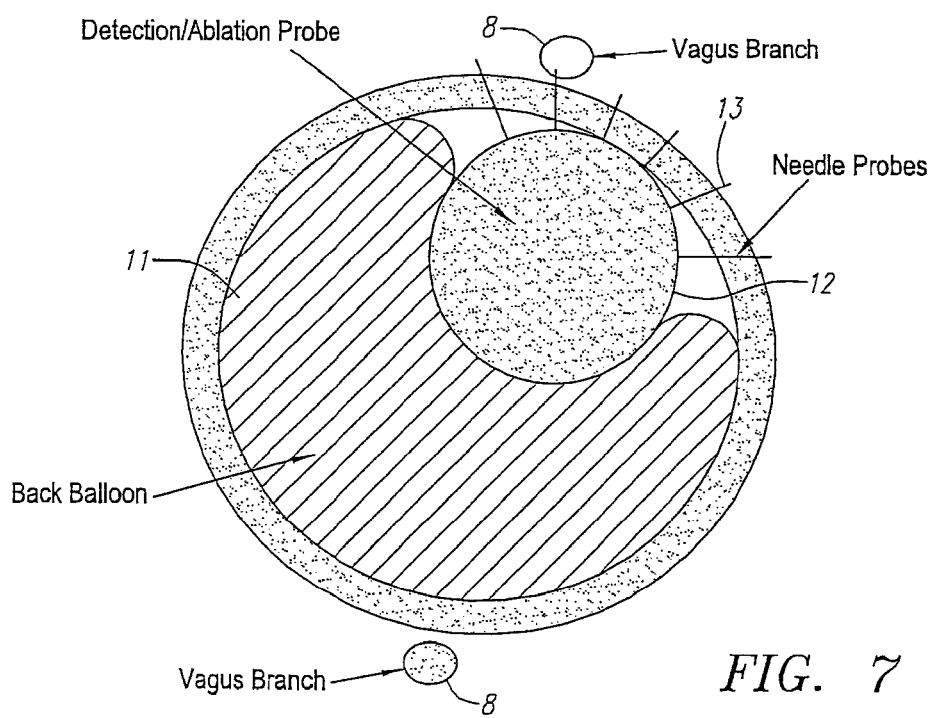
FIG. 7 is an illustration of an ablating device which ablates a sector of the circumference of the outer wall of the esophagus.

In the present invention, the needle probes can irradiate around the complete circumference of the device as shown in FIG. 6 or from only a portion of the device as shown in FIG. 7. If the latter, the device can be rotated sequentially to ensure complete coverage. As further shown in FIG. 7, when the needle probes 13 radiate from only a portion of the circumference of the device 12, a back balloon 11 can be used to position the device 12 in the desired location.

Figure 8:
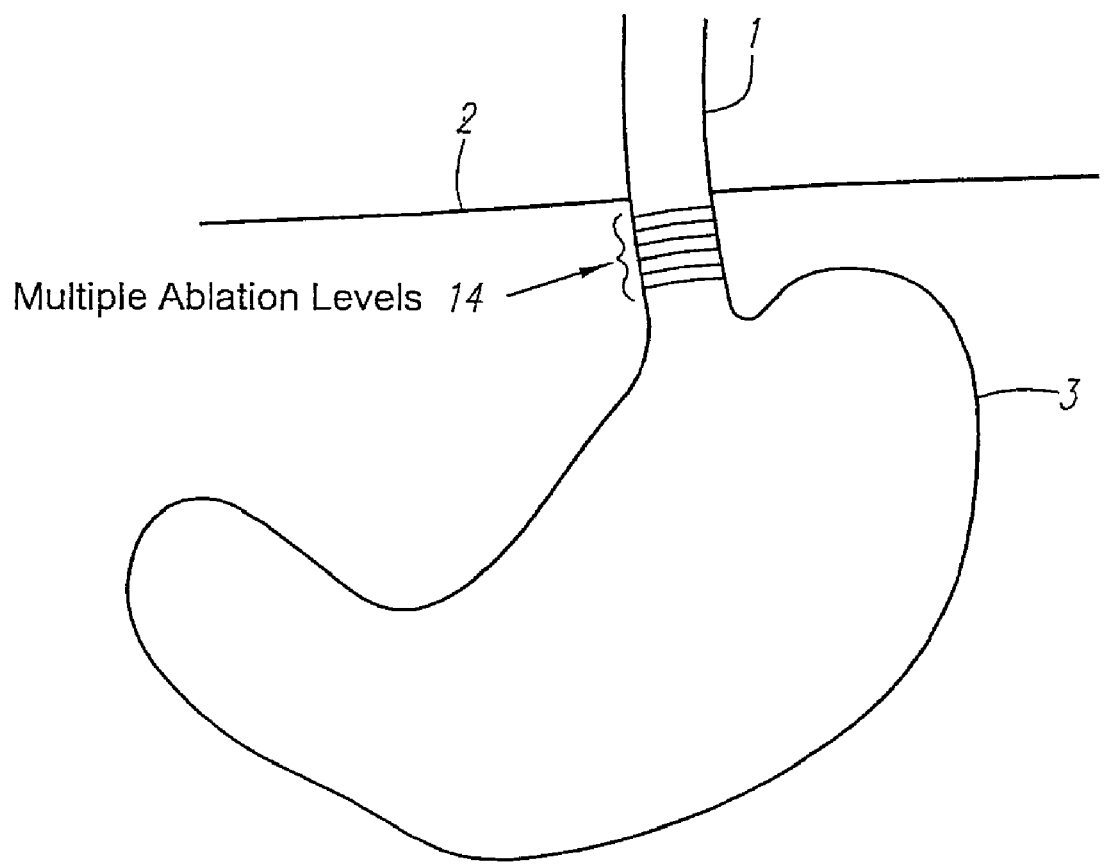
FIG. 8 shows ablating at multiple levels.
Figure 10:
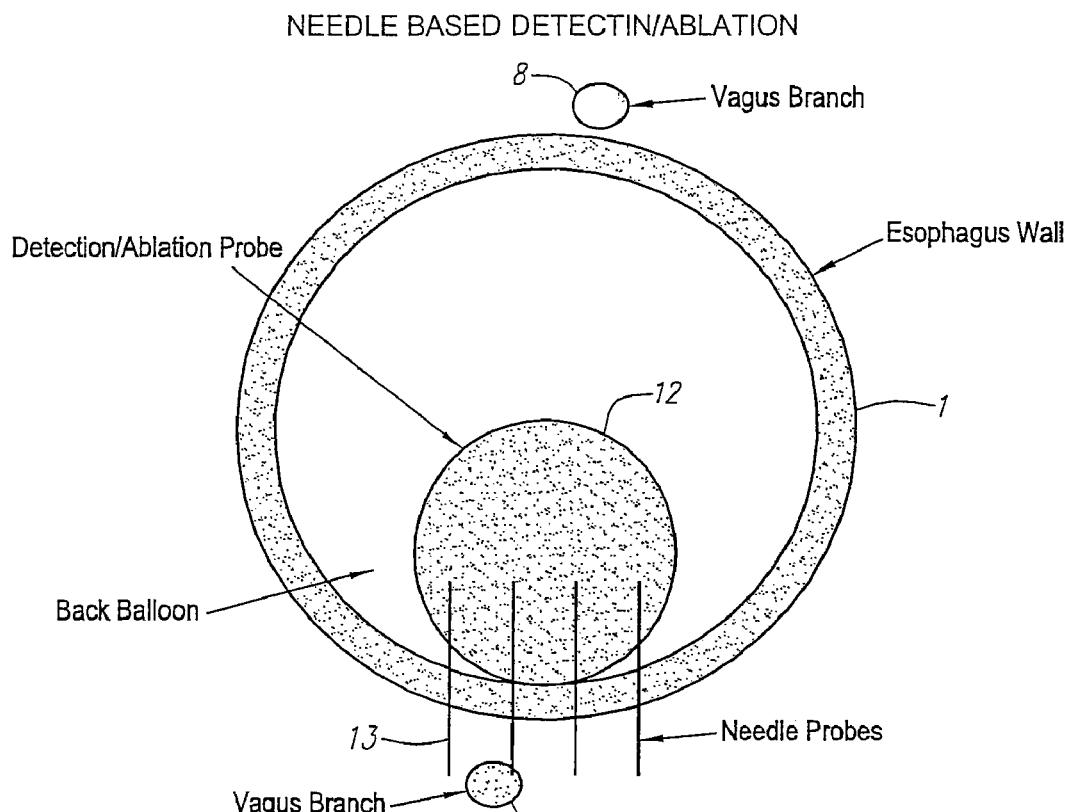
FIG. 10 illustrates the use of still another ablation device to locate and interrupt the vagal nerve.

FIG. 10 illustrates an alternative sector-specific ablation device in which needle probes 13 are activated by device 12 to locate and ablate the vagal nerve in the manner described above. If a patient can obtain the desired benefit of obesity reduction by ablating the two main vagus branches 8, the procedure is simplified and the amount of ablation necessary is reduced. On the other hand, as shown in FIG. 8, if multiple ablation levels 14 are found to be necessary to provide the desired benefit to the patients, more than one ablation can be performed.

Figure 9:
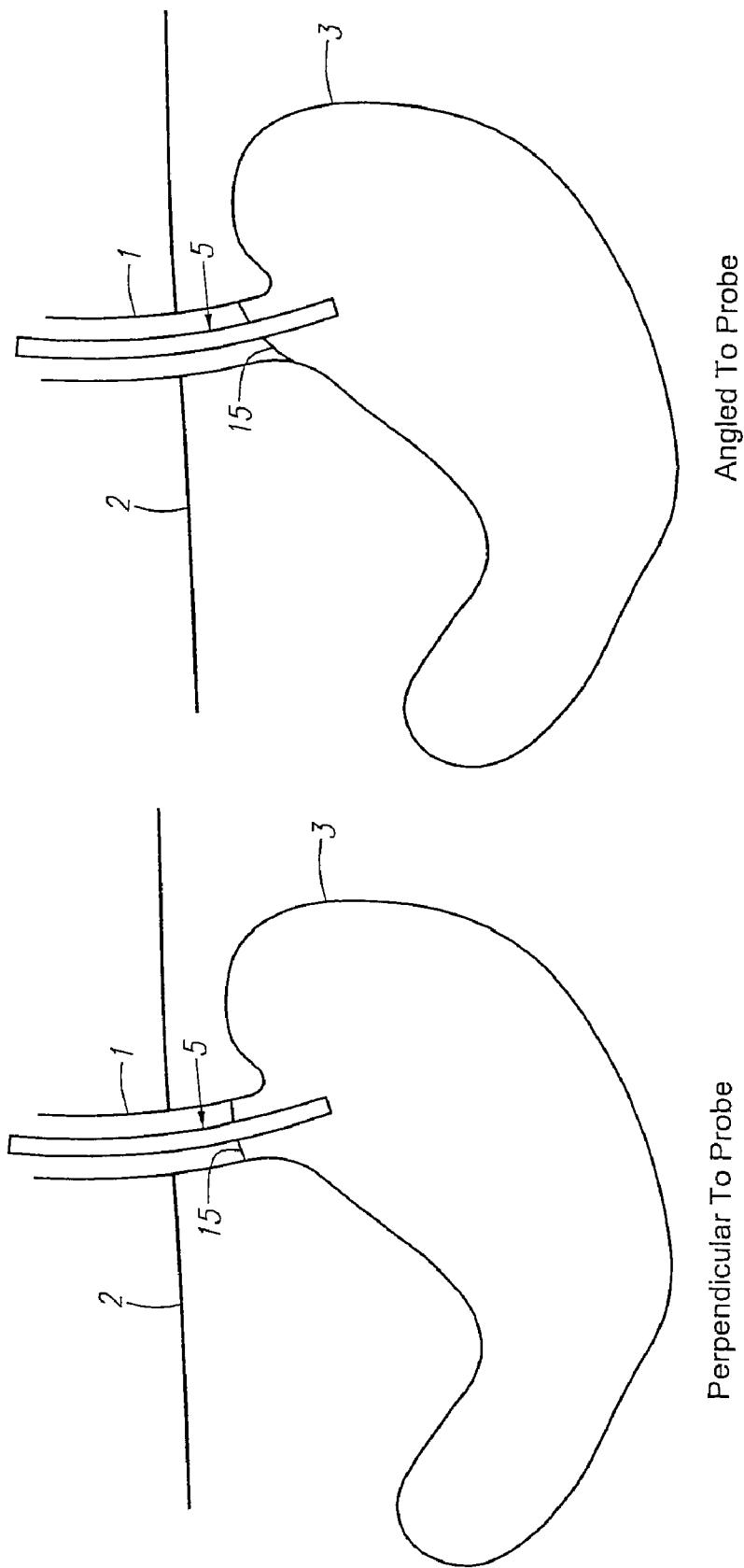
FIG. 9 illustrates an ablation ring which can be adjusted to ablate at different angles relative to the access of the esophagus.

As shown in FIG. 9, if the patient's anatomy makes it desirable, an ablation device 5 can be provided with an energy delivery component 15 which is adjustable such that energy can be delivered perpendicularly to the probe or at an angle to the probe.

Figure 11:
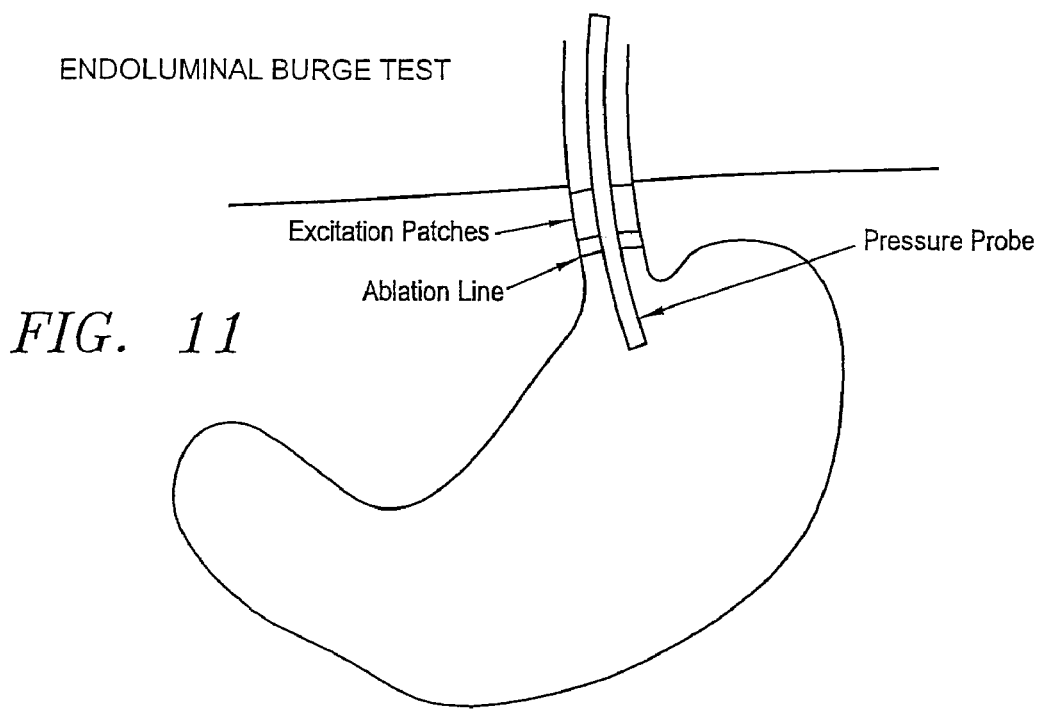
FIG. 11 illustrates an endoluminal burge test which can be used to determine the extent of ablation accomplished.

FIG. 11 illustrates an endoluminal burge test which can be used to determine the extent of ablation accomplished. When a needle probe is used to deliver energy according to the present invention, the device can be provided with temperature sensors such as thermocouples which are disposed in the distal region of the needle probes. The needle probes can be formed of a variety of materials including nickel-titanium alloy. The needle probes can assume a linear or curved shape when deployed. The device may also be provided with means for cooling the treatment site with a suitable fluid such as water, air, or other liquid or gas, to control the temperature at the treatment site. Thus, the temperature sensor can either cause a cooling medium to be provided or shut off the delivery of energy through one or more needle probes.

Figure 12:
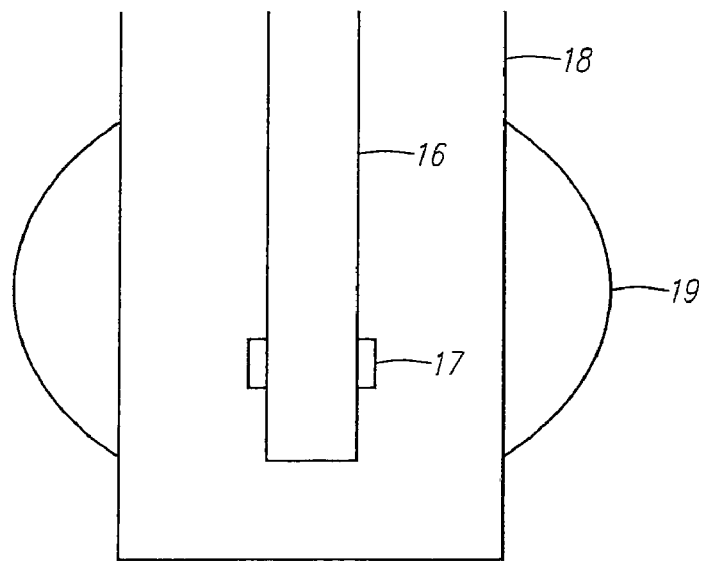
FIG. 12 shows an ultrasound ablating device which may be used according to the present invention.

In a preferred embodiment of the present invention, high intensity focused ultrasound (HIFU) is used to ablate the vagal nerve branches. The HIFU energy can be transmitted transesophageally to ablate the vagal nerves on the outer wall of the esophagus. FIG. 12 illustrates in a diagrammatic form an ultrasound device which can be used according to the present invention. As shown, the device comprises an elongated member 16 which has an ultrasound transducer 17 mounted on its distal region. The elongated member is positioned in a housing 18 which is provided with an inflatable balloon 19. This device may be installed by passing it through the throat and down the esophagus until it reaches its desired location with the balloon 19 deflated. The balloon 19 can then be inflated to position the device and the ultrasound transducer can be activated to transmit energy radially outwardly. Alternatively, a vacuum device can be used to position the housing.

Figure 13:
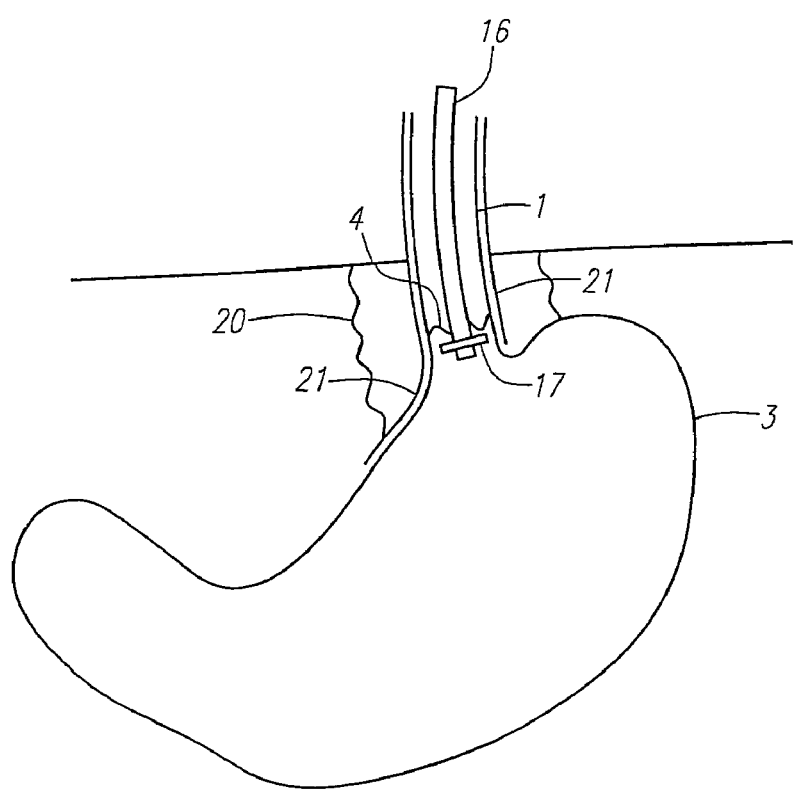
FIG. 13 illustrates an ultrasound device installed in the esophagus.

FIG. 13 is a diagrammatic illustration of an ultrasound transducer installed in the esophagus. As shown in this figure, the transducer device 16 is installed in the esophagus 1 in the region of the Z-line 4. The subhiatal fat ring 20 is also shown. When the transducer 17 is activated, ablating energy will be radiated through the wall of the esophagus to ablate the vagal nerve branches 21 which are also shown diagrammatically.

Figure 14:
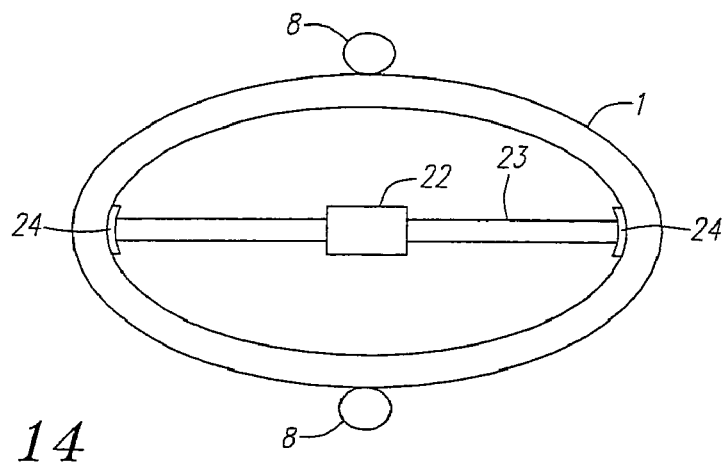
FIG. 14 illustrates an ablation device installed in the esophagus in a manner which shows the esophasgus held in its naturally relaxed configuration by a transducer device.
Figure 15:
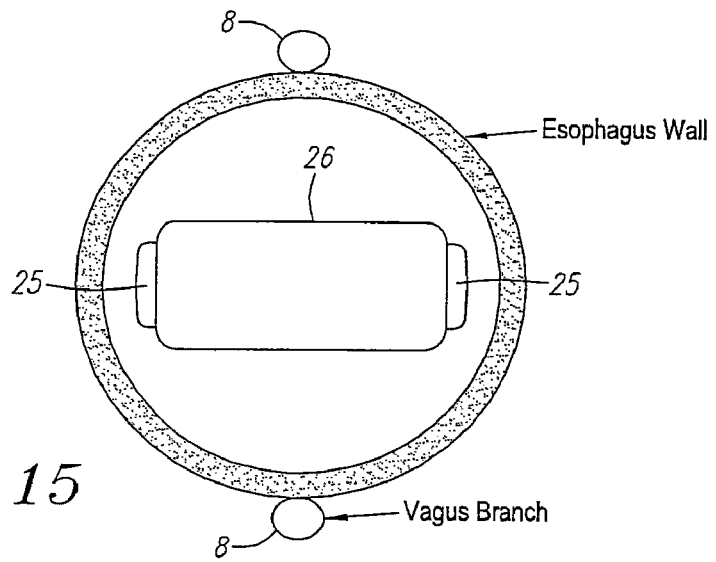
FIGS. 15 and 16 illustrate an alternative to the device shown in FIG. 14.
Figure 16:
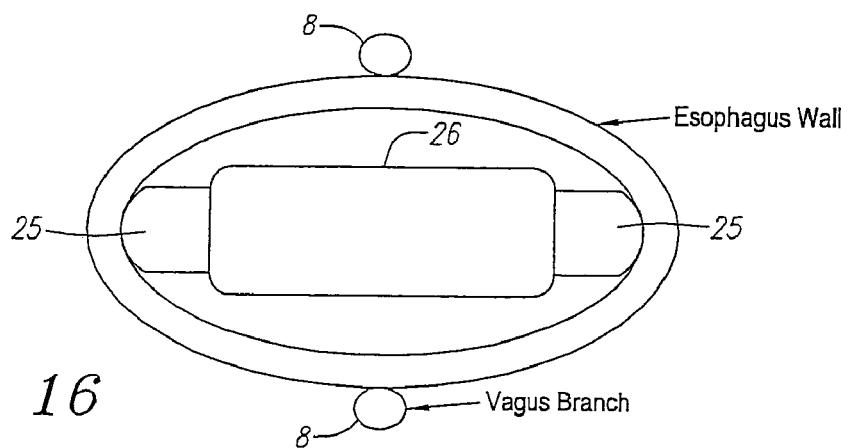

Although the esophagus is generally illustrated anatomically as a generally cylindrical tube, in its relaxed condition it assumes a more elliptical configuration which can be characterized as floppy. In other words, somewhat like a sock before it is put upon a foot, it does not assume a generally circular configuration unless it contains food, but otherwise has a configuration in which the opposing walls of the esophagus are closer together than they would be when in a circular configuration as shown in FIG. 14. In this figure, esophagus 1 with vagal nerve branches 8 on its outer wall is provided with a transducer 22 which has radially extending struts 23. Each of these struts 23 has a rounded portion 24 at its distal end. The struts 23 and 24 serve to hold the esophagus in its relaxed generally elliptical shape and to hold the transducer 22 in the desired location as well. In an alternative embodiment illustrated in FIGS. 15 and 16, balloons 25 mounted on the side of the transducer-containing device 26 are implemented to hold the esophagus in a more ellipitical shape. When these types of devices are used, the transducer device 22 or 26 could be constructed to direct ultrasound energy towards the vagal nerve branches 8 in one direction or in two directions. FIG. 15 shows the balloons 25 in the deflated state and FIG. 16 shows the balloons in the inflated state.

Ultrasound heating technology, including high-intensity ultrasound and HIFU are well understood. For example, Chapter 12, entitled "Ultrasound heating technology," of "Thermo-radiotherapy and Thermo-chemotherapy," vol. 1, edited by Seegenschmiedt, Fessenden and Vernon, contains a thorough explanation of the use of ultrasound in thermal therapy. This chapter is incorporated by reference herein.

The present invention is not to be considered to be limited to the embodiments described above, but is of the full scope of the appended claims.

We claim:

1. A method for reducing obesity by reducing the transmission of a hunger signal through the vagal nerve by transesophageal ablation of the vagal nerve comprising the steps of:
   introducing an ablation energy delivery device into the esophagus through the nose or mouth and positioning said device below the diaphragm,
   ablating at least one vagal nerve branch by transesophageal delivery of ablation energy to the site of the at least one vagal nerve branch on the outer wall of the esophagus wherein transmission of the hunger signal through the at least one vagal nerve branch is prevented.

2. The method of claim 1 wherein the ablation energy is ultrasound.

3. The method of claim 1 wherein the ablation energy is high intensity ultrasound.

4. The method of claim 1 wherein the ablation energy is high intensity focused ultrasound.

5. The method of claim 1 wherein the ablation energy is radio frequency energy.

6. The method of claim 5 further comprising the step of passing electrodes through the wall of the esophagus to the site of the at least one vagal nerve branch.

7. The method of claim 6 wherein the electrodes are used to locate the vagal nerve branches.

8. The method of claim 1 wherein said energy delivery device is introduced into the esophagus through the mouth.

9. The method of claim 1 wherein said energy delivery device is delivered to the esophagus through the nose.

10. The method of claim 1 wherein the step of positioning the device includes maintaining the esophagus in an elliptical cross-sectional shape adjacent the location along the esophagus the ablation energy delivery device is positioned.

11. In an apparatus for ablation of a vagal nerve branch to reduce the transmission of hunger signals through the vagal nerves to reduce obesity comprising an energy delivery device, and a carrier for said energy delivery device, said carrier being adapted to pass through the nose or mouth and locate said energy delivery device in the esophagus, the improvement comprising:
   the energy delivery device being an ablation energy delivery device configured to ablate a vagal nerve branch by transesophageal delivery of ablation energy to the vagal nerve, and
   an actuator configured to energize the ablation energy delivery device with energy sufficient to ablate the vagal nerve branch to prevent transmission of hunger signals through the vagal nerve branch.

12. The apparatus of claim 11 wherein the ablation energy delivery device is an ultrasound transducer.

13. The apparatus of claim 12 wherein said transducer is a high intensity ultrasound transducer.

14. The apparatus of claim 12 wherein said transducer is a high intensity focused ultrasound transducer.

15. The apparatus of claim 11 wherein said energy delivery device is a radio frequency electrode.

16. The apparatus of claim 11 wherein the carrier is provided with a positioning member.

17. The apparatus of claim 16 wherein said positioning member is a balloon.

18. The apparatus of claim 16 wherein said positioning member is a vacuum device.

19. The apparatus of claim 16 wherein said positioning member is configured to maintain the esophagus in an elliptical cross-sectional shape adjacent the ablation energy device.

20. The apparatus of claim 19 wherein said positioning member comprises first and second members opposingly extendible from the carrier.

21. The apparatus of claim 20 wherein the first and second members are balloons.

22. The apparatus of claim 20 wherein the first and second members are struts.

* * * * *